United States Patent [19]

Hajos

[11] Patent Number: 4,603,213

[45] Date of Patent: Jul. 29, 1986

[54] TOTAL SYNTHESIS OF 1RS,4SR,5RS-4-(4,8-DIMETHYL-5-HYDROXY-7-NONEN-1-YL)-4-METHYL-3,8-DIOXABICYCLO[3.2.1]OCTANE-1-ACETIC ACID

[75] Inventor: Zoltan G. Hajos, Princeton, N.J.

[73] Assignee: Ortho Pharmaceutical Corporation, Raritan, N.J.

[21] Appl. No.: 655,474

[22] Filed: Sep. 27, 1984

[51] Int. Cl.[4] .......................................... C07D 319/14
[52] U.S. Cl. .................................................. 549/363
[58] Field of Search ........................................ 549/363

[56] References Cited

U.S. PATENT DOCUMENTS

| | | | |
|---|---|---|---|
| 4,237,054 | 12/1980 | Chen | 549/363 |
| 4,237,055 | 12/1980 | Hajos et al. | 549/363 |
| 4,276,216 | 6/1981 | Hajos et al. | 549/363 |
| 4,284,565 | 8/1981 | Hajos | 549/363 |

*Primary Examiner*—Ethyl G. Love
*Attorney, Agent, or Firm*—Benjamin F. Lambert

[57] ABSTRACT

The synthesis of 1RS,4SR,5RS-4-(4,8-dimethyl-5-hydroxy-7-nonen-1-yl)-4-methyl-3,8-dioxabicyclo[3.2.1]octane-1-acetic acid from its terminal double bond isomer is described. The acetic acid compound is a contragestional agent.

5 Claims, No Drawings

TOTAL SYNTHESIS OF 1RS,4SR,5RS-4-(4,8-DIMETHYL-5-HYDROXY-7-NONEN-1-YL)-4-METHYL-3,8-DIOXABICYCLO[3.2.1]OCTANE-1-ACETIC ACID

U.S. Pat. No. 4,284,565 describes a method for the total synthesis of 1RS,4SR,5RS-4-(4,8-dimethyl-5-hydroxy-7-nonen-1-yl)-4-methyl-3,8-dioxabicyclo[3.2.1]octane-1-acetic acid. The acetic acid compound is a derivative of zoapatanol which is one of the active ingredients in the zoapatle plant and is also active as a utero-evacuant agent. The isolation and structural determination of zoapatanol is described in U.S. Pat. No. 4,086,358.

The zoapatanol derivative has the following structure

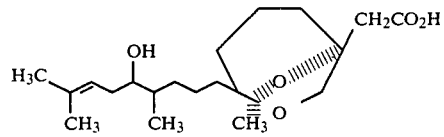

In the preparation of the zoapatanol derivative, the terminal double bond isomer is obtained in addition to the desired compound. The isomers are separated by a tedious process which involves column chromatography over silica gel which is impregnated with silver nitrate. The present invention relates to an improved process for the synthesis of 1RS,4SR,5RS-4-(4,8-dimethyl-5-hydroxy-7-nonen-1-yl)-4-methyl-3,8-dioxabicyclo[3.2.1]octane-2-acetic acid free of the terminal double bond isomer.

The synthesis is comprised of several steps which are summarized in the following schematic diagram:

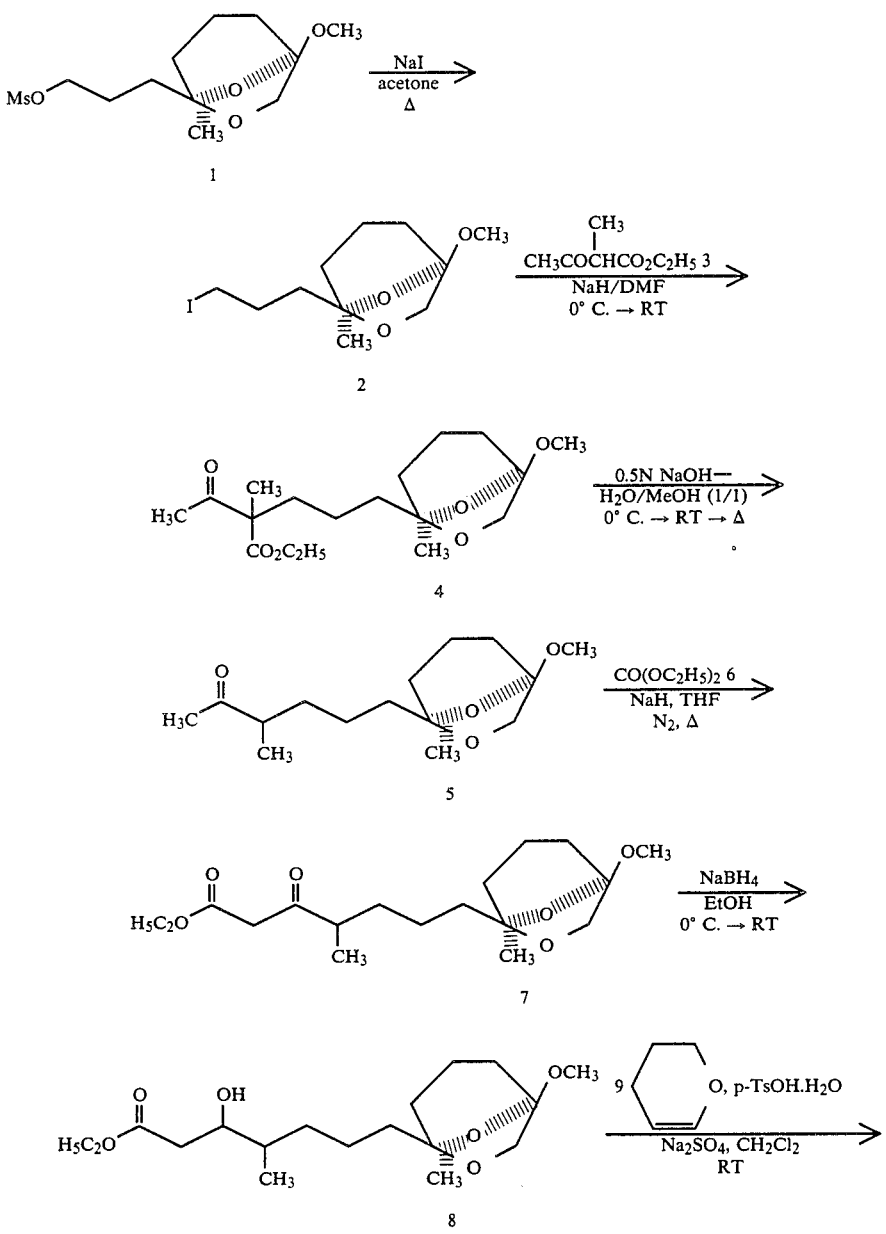

-continued
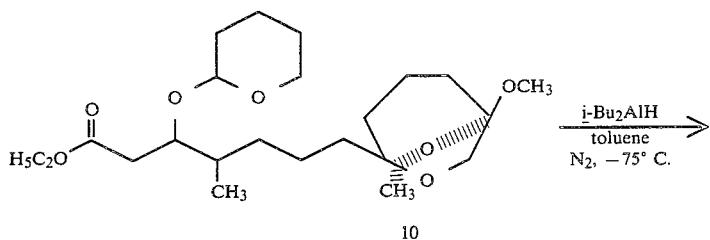
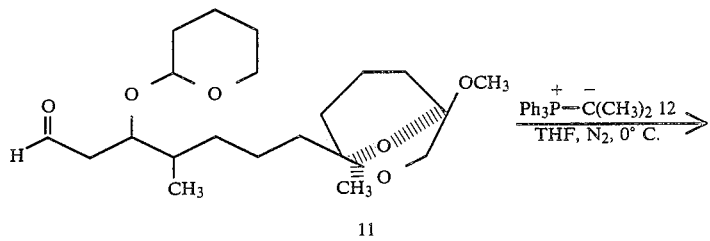
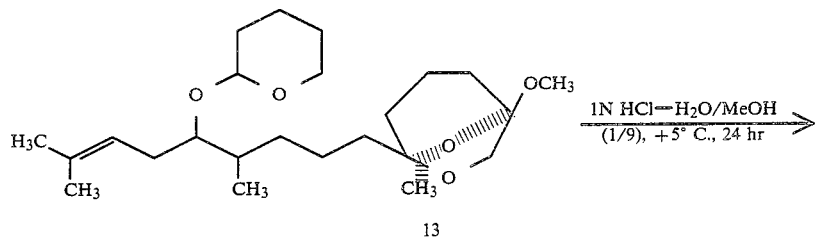
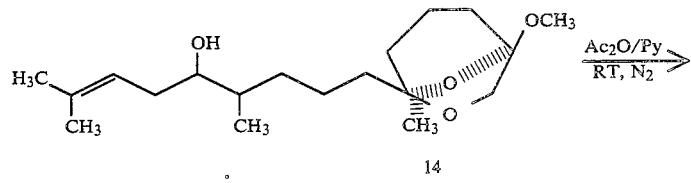
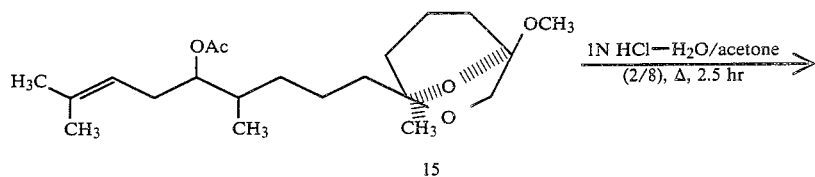
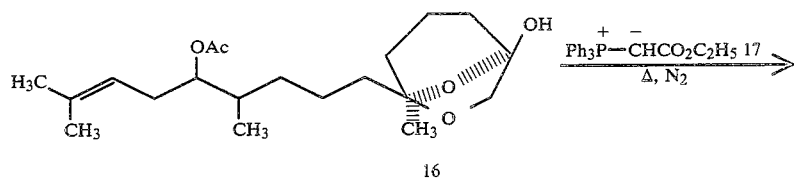
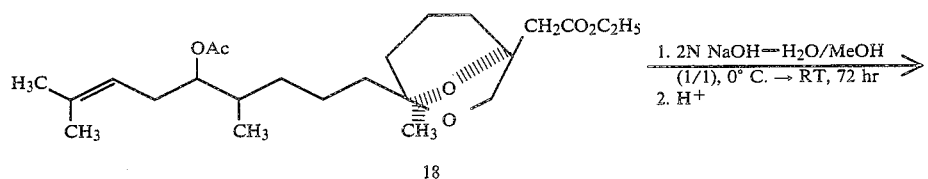

-continued

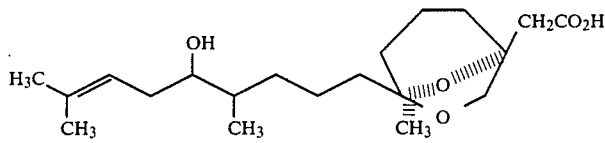

19 wherein Ms is a mesyl group. The products of the reactions in each case are isolated and characterized by techniques known to those skilled in the art.

As can be seen from the diagram, the first step in the synthesis involves the conversion of the bicyclic mesylate (1) to the bicyclic halide (2) by reaction with a metal halide such as sodium iodide, potassium iodide, lithium bromide, copper bromide, lithium chloride or copper chloride in a suitable solvent such as acetone, dioxane or tetrahydrofuran. The reaction can be carried out at room temperature, however, it is preferred to carry the reaction out at the reflux temperature of the solvent. The bicyclic iodide (2) is then converted to the keto ester (4) by reaction with α-methyl acetoacetate in the presence of a base such as sodium hydride, lithium diisopropyl amide, potassium tertiary butoxide and metal alkoxides such as sodium ethoxide. Solvents which can be employed for the reaction include dimethylformamide, tetrahydrofuran, diethyl ether, dimethylformamide and dioxane.

The keto ester (4) is then converted to the ketone (5) by hydrolysis with aqueous base. The hydrolysis reaction can be carried out at a temperature between 0° C. and room temperature. As the base, any alkali metal or alkaline earth metal hydroxide may be employed. Suitable solvents for the reaction include alcohols such as methanol, ethanol and propanol, tetrahydrofuran, dioxane and the like. The ketone (5) is then converted to the keto ester (7) by reaction with a loweralkyl carbonate such as, for example, ethyl or propyl carbonate in a suitable solvent. The reaction is carried out at a temperature between room temperature and 75° C. As the solvent, tetrahydrofuran, dioxane, dimethylformamide and the like may be employed. The keto ester (7) is then reduced to the hydroxy ester (8) by reaction with a reducing agent in a suitable solvent. As the reducing agent sodium borohydride, potassium borohydride, lithium aluminum tritertiarybutoxy hydride and the like may be employed. Suitable solvents for the reaction include alcohols such as methyl alcohol, ethyl alcohol and isopropyl alcohol, tetrahydrofuran and the like. The hydroxy ester (8) is then converted to the corresponding tetrahydropyranyl ether (10) by reaction with dihydropyran in a suitable solvent such as absolute chloroform, methylene chloride, dioxane and tetrahydrofuran. p-Toluenesulfonic acid monohydrate can be employed as the catalyst for the reaction. The tetrahydropyranyl ether is then converted to the corresponding aldehyde (11) by reaction with a reducing agent such as diisobutylaluminum hydride in a suitable solvent such as toluene, ether and hexane. The reaction is carried out at a temperature between −80° C. and 0° C.

The aldehyde (11) is then converted to the olefin (13) by reacting it with a reagent prepared from isopropyl triphenylphosphonium bromide and n-butyllithium. The reaction can be carried out at a temperature between 0° C. and room temperature but it is preferred to carry the reaction out at 0° C. As the solvent tetrahydrofuran, methylene chloride, dioxane, and alcohol free chloroform may be employed. The olefin (13) is then converted to the alcohol (14) by hydrolysis of the tetrahydropyranyl ether with a mineral acid, such as hydrochloric acid, sulfuric acid and phosphoric acid in a suitable solvent such as methanol, tetrahydrofuran and dioxane. The reaction can be carried out at a temperature between 0° C. and room temperature. The acetal alcohol (14) is then converted to the corresponding ester (15) by reaction with an esterifying agent such as acetic anhydride, propionic anhydride butyric anhydride, acetyl chloride, propionyl chloride and the like in the presence of a base such as pyridine, triethylamine and 4-dimethylaminopyridine. As the solvent for the reaction, anhydrous pyridine and dimethylformamide may be employed. Reaction of the alkoxy acetal (15) with aqueous acid in a suitable solvent such as acetone, tetrahydrofuran or dioxane yields the hemiacetal ester (16). As the acid, hydrochloric acid, sulfuric acid or phosphoric acid may be employed. The hemiacetal ester (16) is then converted to the diester (18) by reaction with carbethoxymethylene triphenylphosphorane. The mixture of the two reactants is heated to a melt, preferably under nitrogen, stirred for from several hours to two to four days. The crude product can be purified by column chromatography or by other techniques known to those skilled in the art.

In the final step the diester (18) is converted to the dioxabicyclo[3.2.1]octane-1-acetic acid compound by basic hydrolysis in a suitable solvent such as methanol, ethanol, dioxane or tetrahydrofuran. As the base an alkali metal hydroxide such as sodium or potassium hydroxide can be employed. The reaction is carried out at a temperature between about 0° C.and room temperature. The free acid is isolated from the reaction mixture by techniques known to those skilled in the art. The methyl group at the 4 position and the hydroxy group at the 5 position in the side chain of the free acid are of undefined stereochemistry.

The starting material for the preparation of the zoapatanol derivative, 1RS,4RS,5SR-4-(2-methanesulfonyloxypropyl)-1-methoxy-4-methyl-3,8-dioxabicyclo[3.2.1]-octane is prepared according to the method described in U.S. Pat. No. 4,284,565.

EXAMPLE 1

1RS,4RS,5SR-4-(3-Iodopropyl)-1-methoxy-4-methyl-3,8-dioxabicyclo-[3.2.1]octane

Sodium iodide (2.4 g, 15.92 mM) was added to 1RS,4RS,5SR-4-(2-methanesulfonyloxypropyl)-1-methoxy-4-methyl-3,8-dioxabicyclo[3.2.1]octane (2.34 g, 7.96 mM) in acetone (100 ml). The mixture was stirred and refluxed under nitrogen for 2 hours. It was cooled to room temperature, filtered, the precipitate washed with hexane, and the filtrate evaporated in vacuo. The residue was dissolved in hexane, filtered, evaporated in vacuo to give the bicyclic iodide (1.92 g, 73%). TLC (ether): $R_f$=0.66.

NMR (CDCl$_3$, δ): 3.92 (m, 1H, H̲CO), 3.52 (q, 2H, OCH̲$_2$C(O)OCH$_3$), 3.4 (s, 3H, OCH$_3$), 3.25 (m, 2H, CH̲$_2$I), 1.3 (s, 3H, OCCH$_3$).

EXAMPLE 2

1RS,4RS,5SR-1-Methoxy-4-methyl-4-(4-carbethoxy-4-methyl-5-oxohexyl)-3,8-dioxabicyclo[3.2.1]octane Sodium hydride (405 mg, 8.4 mM of 50% in mineral oil) was washed free of oil with anhydrous n-pentane (2×4 ml). Anhydrous dimethylformamide (6 ml) was added, and the mixture was stirred at 0° C. α-Methyl acetoacetate (1.2 ml, 8.4 mM) in anhydrous dimethylformamide (5 ml) was added to this dropwise within 15 minutes. The resulting mixture was stirred for an additional 30 minutes, and 1RS,4RS,5SR-4-(3-iodopropyl)-1-methoxy-4-methyl-3,8-dixabicyclo[3.2.1]octane (2.4 g, 7.3 mM) in anhydrous DMF (5 ml) was added dropwise, at 0° C. within 10 minutes. The cooling bath was removed, the mixture was stirred at room temperature for 3 hours and then added dropwise to dilute aqueous hydrochloric acid (25 ml ice water and 4.5 ml 2N acid) and methylene chloride (25 ml). The mixture was reextracted with methylene chloride (4×25 ml), washed with aqueous sodium chloride solution, dried (Na$_2$SO$_4$), filtered and evaporated in vacuo to give the keto ester (2.22 g, 89.5%). TLC (10% ether/CH$_2$Cl$_2$). R$_f$=0.39. IR (neat) 1745 (sh), 1718, 1080–1000 cm$^{-1}$.

EXAMPLE 3

1RS,4RS,5SR-4-(4-Methyl-5-oxohexyl)-3,8-dioxabicyclo[3.2.1]octane

Aqueous sodium hydroxide (0.5N 20 ml) was added to 1RS,4RS,5SR-1-methoxy-4-methyl-4-(4-carbethoxy-4-methyl-5-oxohexyl)-3,8-dioxabicyclo[3.2.1]octane (2.195 g, 6.4 mM) in methanol (20 ml) while stirring at 0° C. under nitrogen After 30 minutes at 0° C., the mixture was allowed to come to room temperature and was stirred at room temperature under N$_2$ for 16 hours. After cooling to room temperature the methanol was evaporated in vacuo and the residue was extracted with ether. The ether extract was washed free of base with H$_2$O and NaCl—H$_2$O, dried (Na$_2$SO$_4$) and evaporated in vacuo to give the keto compound (1.585 g, 91.6%). TLC (ether): R$_f$=0.50. IR (neat) 1710, 1095–1000 cm$^{-1}$.

EXAMPLE 4

1RS,4RS,5SR-4-(6-Carbethoxy-4-methyl-5-oxohexyl)-3,8-dioxabicyclo[3.2.1]octane

Dry tetrahydrofuran (THF) (1 ml) and ethyl carbonate (2.34 g, 19.8 mM) in dry THF (4 ml) were added under nitrogen to NaH (480 mg, 10 mM, 50% in mineral oil), washed free of mineral oil with pentane. The resulting suspension was heated to 65° C. and treated dropwise with 1RS,4RS,5SR-4-(4-methyl-5-oxohexyl)-3,8-dioxabicyclo[3.2.1]octane (1.35 g, 5 mM) in dry THF (3 ml). After stirring for 5 minutes, the solution was poured into an ice-cold mixture of 2N HCl (7 ml) in H$_2$O (70 ml) and diethyl ether (50 ml). The resulting mixture was immediately made basic with 10% NaHCO$_3$—H$_2$O. The aqueous layer was extracted with diethyl ether, dried (Na$_2$SO$_4$), filtered and evaporated in vacuo to afford the keto ester, as a yellow oil (1.48 g, 86%). TLC (10% Et$_2$O/CH$_2$Cl$_2$): R$_f$=0.25. IR (neat) 1748, 1715, 1633 cm$^{-1}$.

EXAMPLE 5

1RS,4RS-4-(6-Carbethoxy-5-hydroxy-4-methylhexyl)-3,8-dioxabicyclo[3.2.1]octane

Sodium borohydride (200 mg, 5.26 mM) was added in small portions, within 5 minutes to 1RS,4RS,5SR-4-(6-carbethoxy-4-methyl-5-oxohexyl)-3,8-dioxabicyclo[3.2.1]octane (keto ester) (1.48 g, 4.33 mM) in anhydrous ethyl alcohol (20 ml) while stirring at 0° C. and the resulting mixture was stirred at +5° C. for 16 hours. The mixture was then transferred to a dropping funnel, and added dropwise to a well-stirred mixture of ice water (40 ml), 2N HCl—H$_2$O (5.5 ml) and ether (40 ml). The aqueous portion was reextracted with ether (2×40 ml). The combined ether extracts were evaporated in vacuo. The residue containing ethyl alcohol was dissolved in CH$_2$Cl$_2$, washed with H$_2$O (100 ml), and with NaCl—H$_2$O (100 ml), dried (Na$_2$SO$_4$), filtered, and evaporated in vacuo to give the hydroxy ester (1.48 g, 100%). TLC (10% Et$_2$O/CH$_2$Cl$_2$): R$_f$=0.10. IR (neat) 3600–3300, 1724, 1090–1010 cm$^{-1}$.

EXAMPLE 6

1RS,4RS,5SR-4-(6-Carbethoxy-4-methyl-5-tetrahydropyranyloxyhexyl)-3,8-dioxabicyclo[3.2.1]octane Anhydrous Na$_2$SO$_4$ (1.2 g) and p-toluenesulfonic acid monohydrate (2 mg) were added to 1RS,4RS,5SR-4-(6-carbethoxy-5-hydroxy-4-methylhexyl)-3,8-dioxabicyclo[3.2.1]octane (1.42 g, 4.1 mM) in CH$_2$Cl$_2$ (20 ml) followed by the addition of freshly distilled dihydropyran (0.6 ml, 6.5 mM) while stirring at room temperature under N$_2$. After 2 hours stirring at room temperature, the reaction mixture was added dropwise to a well stirred mixture of ice cold NaHCO$_3$—H$_2$O (10 ml of 1M) and CH$_2$Cl$_2$ (10 ml). The CH$_2$Cl$_2$ extract was washed with H$_2$O (10 ml), NaCl—H$_2$O (10 ml), dried (Na$_2$SO$_4$), and evaporated in vacuo to give the crude ether (1.66 g, 94.6%). Chromatography on 65 g of SilicAR CC-7 using CH$_2$Cl$_2$ (40 ml) and 1% Et$_2$O/CH$_2$Cl$_2$ (2000 ml) eluents gave the purified ether (1.21 g). TLC (1% Et$_2$O/CH$_2$Cl$_2$): R$_f$=0.30. IR (neat) 1724 cm$^{-1}$.

EXAMPLE 7

1RS,4RS,5SR-4-(6-Formyl-4-methyl-5-tetrahydropyranyloxyhexyl)-3,8-dioxabicyclo[3.2.1]octane Diisobutylaluminumhydride in toluene (2.05 ml of 25% w/w, 3.0 mM) was added dropwise within 10 minutes while stirring under nitrogen to 1RS,4RS,5SR-4-(6-carbethoxy-4-methyl-5-tetrahydropyranyloxyhexyl)-3,8-dioxabicyclo[3.2.1]octane (1.195 g, 2.8 mM) in anhydrous toluene (13 ml) at −75° C. The resulting solution was stirred at −75° C. for 2 hours and then added dropwise to a mixture of ice cold saturated NH$_4$Cl—H$_2$O (40 ml) and ethyl ether (40 ml) stirred in an ice bath. The ether was removed and the aqueous layer was reextracted with ether (2×50 ml), and evaporated in vacuo. The residue was taken up in CH$_2$Cl$_2$/H$_2$O. The CH$_2$Cl$_2$ extract was dried (Na$_2$SO$_4$), filtered, and evaporated in vacuo to give the aldehyde (0.94 g, 87.4%). TLC (Et$_2$O): R$_f$=0.63. IR (CHCl$_3$) 1730 cm$^{-1}$.

EXAMPLE 8

1RS,4RS,5SR-1-Methoxy-4-methyl-4-(5-tetrahydropyranyloxy-4,8-dimethyl-7-nonenyl)-3,8-dioxabicyclo[3.2.1]octane A. Preparation of the ylide: n-Butyl lithium (1.46 ml of 2.3M in hexane=3.36 mM) was added to a suspension of isopropyl triphenylphosphonium bromide (987 mg, 2.57 mM) in THF (2.2 ml) under nitrogen while stirring at room temperature. The reaction mixture was stirred at room temperature for 3 hours to form the ylide which was used without isolating it in step B.

B. Wittig reaction: The deep red solution of the ylide was added while stirring at 0° C. under nitrogen to a solution of the aldehyde obtained in Example 7 (379.2 mg, 0.98 m) in THF (1.1 ml). The solution was stirred at 0° C. for 16 hours, poured into ice-$H_2O$, and extracted with ether. The ether extract was washed (NaCl/$H_2O$, and $H_2O$), and evaporated in vacuo to an amorphous solid. The solid was dissolved in $CH_2Cl_2$, dried ($Na_2SO_4$), filtered, and evaporated in vacuo. The amorphous solid (820 mg) obtained was extracted with hexane to give the title olefin as a yellow oil (437 mg, 100%). TLC (4 $Et_2O$/6 $CH_2Cl_2$) $R_f$=0.58; IR (neat) 1420, 1090, 1075, 1020, 830, 813 cm$^{-1}$.

EXAMPLE 9

1RS,4RS,5SR-1-Methoxy-4-methyl-4-(5-hydroxy-4,8-dimethyl-7-nonenyl)-3,8-dioxabicyclo[3.2.1]octane 1N HCl—$H_2O$ (1 ml) was added to 1RS,4RS,5SR-1-methoxy-4-methyl-4-(5-tetrahydropyranyloxy-4,8-dimethyl-7-nonenyl)-3,8-dioxabicyclo[3.2.1]octane (402 mg, 0.98 mM) in methanol (9 ml) while stirring at 0° C. The mixture was stirred at +5° C. for 16 hours, and then added to ice cold saturated $NaHCO_3$—$H_2O$ (2 ml). The methanol was evaporated in vacuo, and the residue extracted with $CH_2Cl_2$. The extract was washed with NaCl—$H_2O$, dried ($Na_2SO_4$), filtered, and evaporated in vacuo to give the acetal alcohol (331.4 mg, 100%). TLC ($Et_2O$/$CH_2Cl_2$=4/6 $R_f$=0.62. IR (neat) 3400–3200, 1090–1030 cm$^{-1}$.

EXAMPLE 10

1RS,4RS,5SR-1-Methoxy-4-methyl-4-(5-acetoxy-4,8-dimethyl-7-nonenyl)-3,8-dioxabicyclo[3.2.1]octane A mixture of anhydrous pyridine (1.0 ml) and acetic anhydride (2.0 ml) was added to the acetal alcohol obtained in Example 9 (311.4 mg, 0.96 mM) at room temperature for 72 hours, and then evaporated while stirring under high vacuum at 45° C. for 1 hour. The residue was dissolved in $CH_2Cl_2$, washed with NaCl—$H_2O$, dried ($Na_2SO_4$), filtered and evaporated in vacuo to give the acetate (311.5 mg, 100%). TLC (10% ether in $CH_2Cl_2$): $R_f$=0.65. IR (neat) 1730, 1242, 1090–1030 cm$^{-1}$.

EXAMPLE 11

1RS,4RS,5SR-1-Hydroxy-4-methyl-4-(5-acetoxy-4,8-dimethyl-7-nonenyl)-3,8-dioxabicyclo[3.2.1]octane 1N HCl—$H_2O$ (4 ml) was added to the acetoxy acetal obtained in Example 10 (676.2 mg, 1.84 mM) in acetone (16 ml) while stirring at room temperature. The mixture was stirred and refluxed under nitrogen for 2.5 hours. The acetone was evaporated in vacuo. The residue was extracted with $CH_2Cl_2$, washed with $H_2O$, NaCl—$H_2O$, dried ($Na_2SO_4$), filtered, and evaporated in vacuo to give the hemiacetal acetate (677 mg, 100%). TLC (10% ether in $CH_2Cl_2$): $R_f$=0.15. IR (neat) 3330, 1725, 1242 cm$^{-1}$.

EXAMPLE 12

Ethyl(1RS,4SR,5RS)-4-(5-acetoxy-4,8-dimethyl-7-nonenyl)-4-methyl-3,8-dioxabicyclo[3.2.1]octane-1-acetate (Carbethoxymethylene)triphenylphosphorane (1.3 g, 3.8 mM) was added to the hemiacetal acetate obtained in Example 11 (677 mg, 1.9 mM). The mixture was heated to melt under $N_2$ to 120° C., stirred at this temperature for two days and then cooled to room temperature. Additional triphenylphosphorane (650 mg, 1.87 mM) was added, and the mixture was heated with stirring at 120° C. for two more days. The reaction mixture was cooled to room temperature, and extracted with ether ($\sim$50 ml) two times to give the crude acetate ester (1.31 g).

The crude acetate ester and another preparation of similar quality were combined (1.86 g) and purified by column chromatography (90 g, SilicAR CC-7, $CH_2Cl_2$ and 1% ether in $CH_2Cl_2$ eluents) to give the pure acetate ester (347 mg, 31.5%). TLC ($Et_2O$): $R_f$=0.75. IR (neat) 1725, 1242 cm$^{-1}$.

EXAMPLE 13

1RS,4SR,5RS-4-(4,8-Dimethyl-5-hydroxy-7-nonen-1-yl)-4-methyl-3,8-dioxabicyclo[3.2.1]octane-1-acetic acid 2N NaOH—$H_2O$ (5 ml) was added to the acetate ester obtained in Example 12 (347 mg, 0.82 mM) in methanol (5 ml) while stirring at 0° C. under nitrogen. After 10 minutes, the mixture was allowed to come to room temperature and stirred under nitrogen for 72 hours. The methanol was evaporated in vacuo at room temperature and the residue was extracted with ether. The aqueous basic solution was cooled to 0° C., stirred, and acidified with 6N HCl—$H_2O$, and extracted with ether. The ether extract was washed with saturated NaCl—$H_2O$, dried ($Na_2SO_4$), filtered, and evaporated in vacuo to give the hydroxy acid (295 mg, 100%), as a thick, light yellow oil.

TLC (20 ether, 2 petroleum ether, 1 AcOH, 20% $AgNO_3$ impregnated silica gel plate, developed two times): $R_f$=0.37. No trace of the double bond isomer ($R_f$=0.26). IR (neat 3550–3330, 2500–200, 1720, 1090–1030 cm$^{-1}$. NMR ($CDCl_3,\delta$): 5.87 (m, 2H, CHOH and $CO_2H$), 5.17 (m, 1H, $(CH_3)_2C=\overline{CH}$), 3.95 (m, 1$\overline{H}$, $\overline{HCO}$), 3.63 (q, J=11 Hz, 2H, $OCH_2\overline{C(O)CH_2}$), 2.67 (s, $\overline{2H}$, $\underline{CH_2CO_2H}$), 1.75 and 1.6$\overline{7}$ (2 br s, 6H, $(\underline{CH_3})_2C=CH$), 1.37 (s, 3H, $\underline{CH_3}CO$), 0.92 (d, J=7 Hz, 3$\overline{H}$, $\underline{CH_3}CH$). GC/MS of bis-$\overline{TMS}$ derivatives: M+ 498; BP=73.

PREPARTION OF STARTING MATERIAL

1RS,4RS,5SR-4-(2-Methanesulfonyloxypropyl)-1-methoxy-4-methyl-3,8-dioxabicyclo[3.2.1]octane(8b)

Triethylamine (4.0 ml, 27 mM distilled, stored over $CaH_2$) is added to 1RS,RS,5Sr-4-(2-hydroxyethyl)-1-methoxy-4-methyl-3,8-dioxabicyclo[3.2.1]octane (2.94 g, 13.6 mM) in $CH_2Cl_2$ (30 ml). The resultant mixture is cooled with ice water, stirred under nitrogen and methanesulfonyl chloride (1.8 ml, 22.40 mM) is added dropwise within five minutes. The reaction mixture is stirred at 5° C., under nitrogen for sixteen hours and then added dropwise to a stirred mixture of ice water (30 ml) and 2N HCl—H₂O (4.0 ml). The organic layer is separated, washed with saturated NaCl—H₂O (2×20 ml), dried with Na₂SO₄, filtered, and evaporated in vacuo to give 1RS,4RS,5SR-2-(2-methanesulfonyloxypropyl)-1-methoxy-4-methyl-3,8-dioxabicyclo[3.2.1]octane (3.29 g, 82.3%).

TLC (ether): $R_f$=0.4. IR (neat): 1330, 1190, 1150, 1090, 1060 cm⁻¹. NMR (CDCl₃,δ): 4.23 (m, 2H, CH₃SO₂O—CH₂—CH₂—), 3.87 (t, 1H,

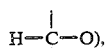

3.53 (q, 2H,

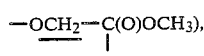

3.02 (s, 3H, CH₃SO₂O—). GC/MS: M⁺(294), M⁺ —C₂H₅ ₂O=264, BP=86

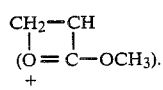

I claim:

1. The process for the preparation of a compound of the formula

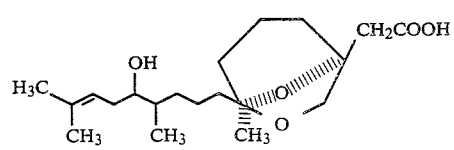

which comprises reacting a compound of the formula

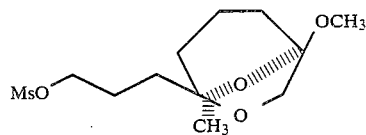

with an alkali metal halide to form a bicyclic halide of the formula

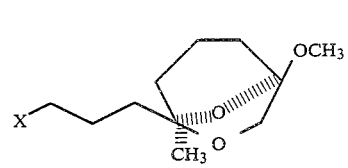

reacting the bicyclic halide with α-methyl acetoacetate in the presence of a first base to form a keto ester of the formula

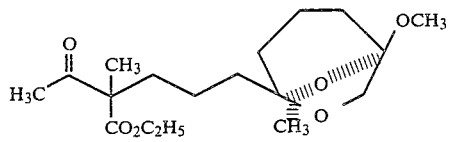

hydrolyzing the keto ester with an alkaline earth or alkali metal hydroxide to form a ketone of the formula

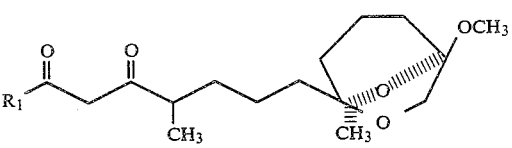

reacting the ketone with an alkyl carbonate in the presence of a second base to form a keto-ester of the formula

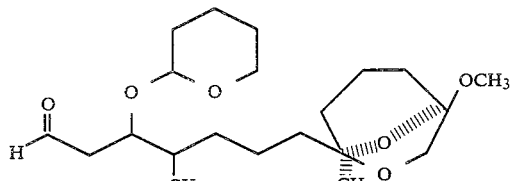

reacting the keto-ester with a reducing agent to form an hydroxy ester of the formula

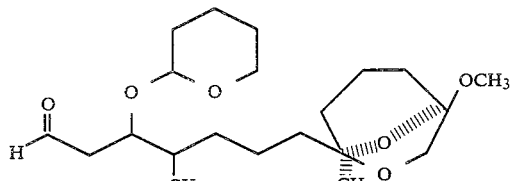

reacting the hydroxy ester with dihydropyran to form a tetrahydropyranyl ether of the formula

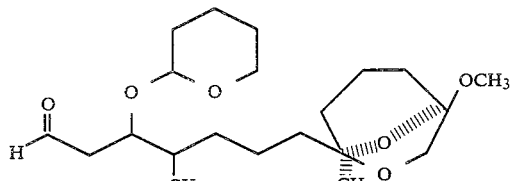

reacting the ester with a reducing agent to form an aldehyde of the formula

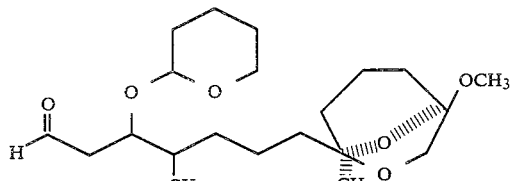

reacting the aldehyde with a reagent formed by reacting isopropyl triphenylphosphonium bromide with n-butyllithium to form a pyranyl ether of the formula hydrolyzing the pyranyl ether with an acid to form an acetal alcohol of the formula

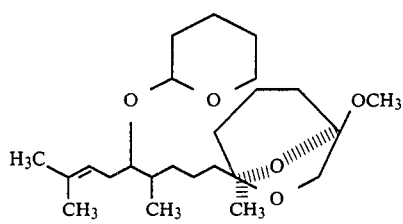

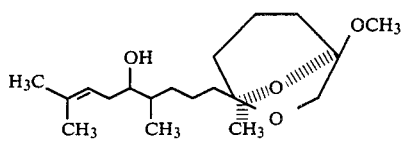

esterifying the acetal alcohol with an esterifying agent to form an ester of the formula

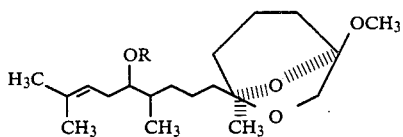

reacting the ester with an acid to form a hemiacetal ester of the formula

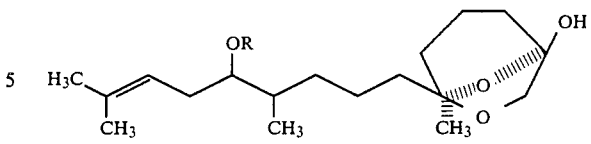

reacting the hemiacetal ester with (carbethoxymethylene) triphenylphosphorane to give a diester of the formula

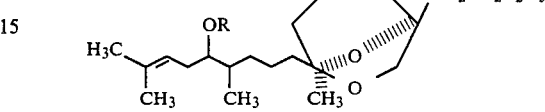

and hydrolyzing the diester with an aqueous base, wherein Ms is a mesyl group and R is lower alkanoyl and $R_1$ is lower alkoxy.

2. The process of claim 1 wherein the alkali metal hydroxide is sodium hydroxide and the metal halide is selected from sodium iodide, lithium bromide and copper chloride.

3. The process of claim 1 wherein the first reducing agent is selected from sodium borohydride, potassium borohydride and lithium aluminum tritertiarybutoxy hydride and the second base and the aqueous base are selected from the alkali metal and alkaline earth metal hydroxides.

4. The process of claim 1 wherein the second reducing agent is diisobutylaluminium hydride.

5. The process of claim 1 wherein the acid is hydrochloric acid, the first base is sodium hydride and the second base is aqueous methanolic sodium hydroxide.

* * * * *